US00PP23169P2

(12) United States Plant Patent
Bergman

(10) Patent No.: US PP23,169 P2
(45) Date of Patent: Nov. 6, 2012

(54) ***CHRYSANTHEMUM* PLANT NAMED 'CIDZ0011'**

(50) Latin Name: *Chrysanthemum×morifolium*
Varietal Denomination: CIDZ0011

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,714

(22) Filed: Aug. 9, 2011

(51) Int. Cl.
*A01H 5/00* (2006.01)

(52) U.S. Cl. ..... Plt./286

(58) Field of Classification Search ..... Plt./286, Plt./297
See application file for complete search history.

(56) References Cited

U.S. PATENT DOCUMENTS

PP17,860 P2 * 7/2007 Bergman ..... Plt./286
PP20,547 P2 * 12/2009 Bergman ..... Plt./286

* cited by examiner

*Primary Examiner* — Howard Locker
(74) *Attorney, Agent, or Firm* — Joshua L. Price

(57) ABSTRACT

A new *Chrysanthemum* plant named 'CIDZ0011' particularly distinguished by the red-purple ray floret color, dark yellow-green foliage, excellent flowering uniformity, good branching and a nine week flowering response.

1 Drawing Sheet

Latin name of the genus and species of the plant claimed: *Chrysanthemum×morifolium.*

Varietal denomination: 'CIDZ0011'.

BACKGROUND OF THE NEW PLANT

The present invention comprises a new *Chrysanthemum*, botanically known as *Chrysanthemum×morifolium*, and hereinafter referred to by the variety name 'CIDZ0011'.

'CIDZ0011' is a product of a planned breeding program. The new cultivar has red-purple ray floret color, dark yellow-green foliage, excellent flowering uniformity, good branching and a nine week flowering response.

'CIDZ0011' originates as a natural whole plant mutation of 'Pink Yosonoma', U.S. Plant Pat. No. 20,547. 'CIDZ0011' was discovered and selected by the inventor as a single flowering plant within a population of the parent cultivar in a controlled breeding program in Fort Myers, Fla., USA in December 2007. The parent cultivar 'Pink Yosonoma' has more of a red-purple ray floret color than that of 'CIDZ0011'.

The first act of asexual reproduction of 'CIDZ0011' was accomplished when vegetative cuttings were propagated from the initial selection in March 2008, in a controlled environment in Fort Myers, Fla., USA.

BRIEF SUMMARY OF INVENTION

Horticultural examination of plants grown from cuttings of the plant initiated in March 2008, and continuing thereafter, has demonstrated that the combination of characteristics as herein disclosed for 'CIDZ0011' are firmly fixed and are retained through successive generations of asexual reproduction.

'CIDZ0011' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7069). 'CIDZ0011' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0011' with colors being as true as possible with an illustration of this type. The photographic drawing shows four flowering potted plants of the new variety, and a close-up of the flowers.

DETAILED BOTANICAL DESCRIPTION

The plant descriptions, measurements and aforementioned photographs were taken in Gilroy, Calif. in mid-May 2011 under natural light. These plants were propagated and grown in Nipomo, Calif. and shipped to Gilroy for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0011' AND A MOST SIMILAR VARIETY

| | 'CIDZ0011' | 'Yosonoma' (U.S. Plant Pat. No. 17,860) |
|---|---|---|
| Ray floret color: | Red-purple | Purple |
| Foliage color: | Little lighter | Little darker |

TABLE 1-continued

DIFFERENCES BETWEEN THE NEW VARIETY 'CIDZ0011' AND A MOST SIMILAR VARIETY

| | 'CIDZ0011' | 'Yosonoma' (U.S. Plant Pat. No. 17,860) |
|---|---|---|
| Quantity of ray florets: | 40-52 | 34 |
| Quantity of disc florets: | Approximately 200 | Approximately 143 |

Plant:
- *Form, growth and habit*.—Herbaceous pot-type, stems upright, good branching, excellent flowering uniformity.
- *Plant height*.—22.0-24.0 cm.
- *Plant height* (*inflorescence included*).—29.0-32.0 cm.
- *Plant width*.—30.0 cm.

Roots:
- *Number of days to initiate roots*.—About 4 days at about 22 degrees C.
- *Number of days to produce a rooted cutting*.—About 10 days at 22 degrees C.
- *Type*.—Fine, fibrous, free branching.
- *Color*.—RHS N155B but whiter.

Foliage:
- *Arrangement*.—Alternate, simple.
- *Immature, leaf color, upper surface*.—RHS 147A.
- *Immature, leaf color, lower surface*.—RHS 137B.
- *Mature, leaf color, upper surface*.—RHS 147A.
- *Mature, leaf color, lower surface*.—RHS 137B.
- *Length*.—7.1-8.8 cm.
- *Width*.—4.5-5.0 cm.
- *Shape*.—Elliptical.
- *Base shape*.—Attenuate.
- *Apex shape*.—Mucronulate.
- *Margin*.—Palmately lobed; irregularly serrate.
- *Texture, upper surface*.—Bifid T-shaped hairs.
- *Lower surface*.—Bifid T-shaped hairs.
- *Color of veins, upper surface*.—Between RHS 138B and RHS 138C.
- *Color of veins, lower surface*.—Between RHS 138B and RHS 138C.
- *Petiole color*.—Between RHS 138B and RHS 138C.
- *Petiole length*.—1.3-1.5 cm.
- *Petiole diameter*.—0.25-0.3 cm.
- *Petiole texture*.—Bifid T-shaped hairs.
- *Length*.—1.3-1.5 cm.
- *Diameter*.—0.25-0.3 cm.
- *Texture*.—Bifid T-shaped hairs.

Stem:
- *Quantity of main branches per plant*.—5-6.
- *Color of stem*.—RHS 143A but appears lighter due to hairs.
- *Length of stem*.—20.0-23.0 cm.
- *Diameter*.—0.5 cm.
- *Length of internodes*.—0.5-2.5 cm.
- *Texture*.—Bifid T-shaped hairs.
- *Color of peduncle*.—RHS 143A but appears lighter due to hairs.
- *Length of peduncle*.—8.5-11.0 cm.
- *Peduncle diameter*.—0.2-0.3 cm.
- *Texture*.—Bifid T-shaped hairs.

Inflorescence:
- *Type*.—Compositae type, solitary daisy-type inflorescences, borne terminally above foliage, ray florets arranged acropetally on a capitulum.
- *Quantity of short days to flowering* (*response time*).—Approximately 9 weeks.
- *Quantity of inflorescences per plant*.—25-30.
- *Lastingness of individual blooms on the plant*.—About 4 weeks.
- *Fragrance*.—Slightly spicy.

Bud (just before opening/showing color):
- *Color*.—Between RHS N78C and RHS N78D but greyer.
- *Length*.—1.5-1.7 cm.
- *Width*.—0.9-1.1 cm.
- *Shape*.—Oblate.

Immature inflorescence:
- *Diameter*.—5.0-6.0 cm.
- *Color of ray florets, upper surface*.—Between RHS 70A and RHS 70B but a brighter shade.
- *Lower surface*.—About RHS 70D but a little lighter.

Mature inflorescence:
- *Diameter*.—9.0-11.0 cm.
- *Depth*.—2.0 cm.
- *Total diameter of disc*.—1.7 cm.
- *Receptacle height*.—0.5 cm.
- *Receptacle diameter*.—0.8 cm.

Ray florets:
- *Average quantity of florets*.—40-52 in 3-4 whorls.
- *Color of florets, upper surface*.—Between RHS 70A and RHS 70B but a brighter shade, some with a little darker apex; fading to shades of RHS 70B with more white at the base.
- *Lower surface*.—About RHS 70D but a little lighter.
- *Length*.—3.7-4.5 cm.
- *Width*.—0.7-0.85 cm.
- *Shape*.—Elliptical.
- *Apex shape*.—Obtuse or acute.
- *Margin*.—Entire.
- *Texture, upper surface*.—Papillose.
- *Lower surface*.—Papillose.

Disc florets:
- *Average quantity of florets*.—Approximately 200.
- *Color of florets*.—Immature: RHS 4D with RHS N144A apex. Mature: RHS 4D with RHS 2B apex.
- *Length*.—0.5-0.6 cm.
- *Width*.—0.1 cm.
- *Shape*.—Tubular, elongated.
- *Apex shape*.—Acute, 5 pointed.

Phyllaries:
- *Quantity*.—30-35.
- *Color, upper surface*.—RHS 137B.
- *Lower surface*.—RHS 137A but appears lighter due to hairs.
- *Length*.—0.5-0.6 cm.
- *Width*.—0.15-0.2 cm.
- *Shape*.—Lanceolate.
- *Apex shape*.—Acute.
- *Base*.—Fused.
- *Margins*.—Entire, some slightly papery.
- *Texture, upper surface*.—Glabrous.
- *Lower surface*.—Bifid T-shaped hairs.

Reproductive organs:
- *Pistil*.—1.
- *Found on both florets*.—Yes.
- *Length*.—0.5 cm.
- *Style color*.—RHS 1B.
- *Style length*.—0.4 cm.
- *Stigma color*.—RHS 3A.

*Stigma shape*.—Bi-parted.
*Ovary color*.—Not observed.
*Stamens*.—4.
*Found on only disc florets*.—Yes.
*Color of filaments*.—RHS 155D.
*Length filaments*.—0.2 cm.
*Anther color*.—Not observed/too overly mature.
*Anther length*.—0.1 cm.
*Anther shape*.—Oblong.
*Color of pollen*.—Not observed.
*Pollen amount*.—Not observed.
*Fertility/seed set*.—Has not been observed on this hybrid.
*Disease/pest resistance*.—Has not been observed on this hybrid.

What is claimed is:

1. A new and distinct variety of *Chrysanthemum* plant named 'CIDZ0011' substantially as illustrated and described herein.

* * * * *

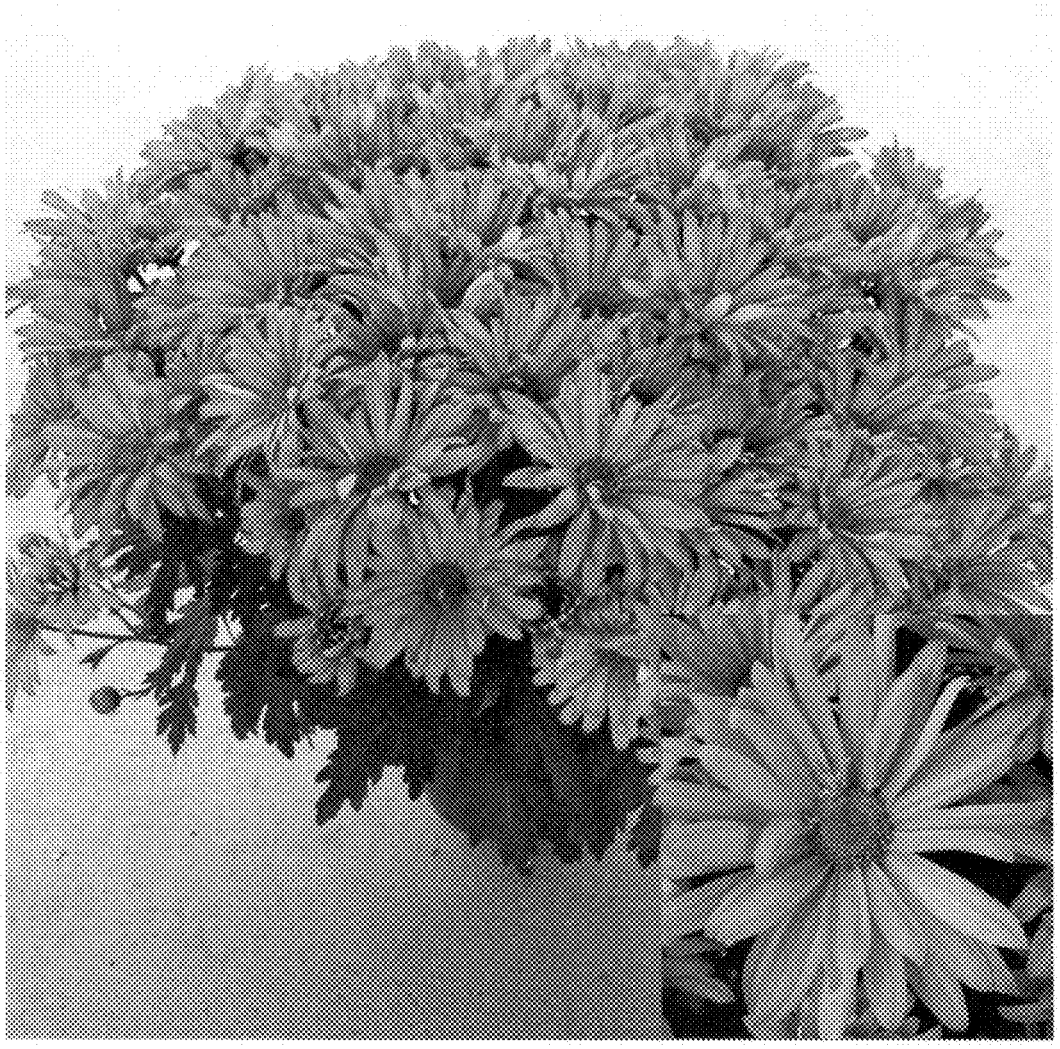

UNITED STATES PATENT AND TRADEMARK OFFICE

CERTIFICATE OF CORRECTION

PATENT NO. : PP23,169 P2
APPLICATION NO. : 13/136714
DATED : November 6, 2012
INVENTOR(S) : Bergman It is certified that error appears in the above-identified patent and that said Letters Patent is hereby corrected as shown below:

At column 3, please remove the following at lines 47-49:
Length - 1.3-1.5 cm
Diameter - 0.25-0.3 cm
Texture - Bifid T-shaped hairs Signed and Sealed this
Twenty-fifth Day of December, 2012

David J. Kappos

David J. Kappos
*Director of the United States Patent and Trademark Office*